US006977079B2

(12) United States Patent
Nagaraja et al.

(10) Patent No.: US 6,977,079 B2
(45) Date of Patent: Dec. 20, 2005

(54) AVIAN PNEUMOVIRUS VACCINE

(75) Inventors: Kakambi Nagaraja, St. Paul, MN (US); Richard Bennett, St. Paul, MN (US); David Halvorson, St. Paul, MN (US); Moses Kariuki Njenga, Woodbury, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 10/346,542

(22) Filed: Jan. 17, 2003

(65) Prior Publication Data

US 2004/0142004 A1 Jul. 22, 2004

(51) Int. Cl.$^7$ ............................................. A61K 39/155
(52) U.S. Cl. ................................ 424/211.1; 424/204.1; 435/69.1; 435/235.1; 435/236
(58) Field of Search ........................... 424/211.1, 204.1; 435/69.1, 235.1, 236

(56) References Cited

U.S. PATENT DOCUMENTS

| | | |
|---|---|---|
| 4,559,229 A | 12/1985 | Page et al. |
| 4,908,305 A | 3/1990 | Snyder |
| 4,946,778 A | 8/1990 | Ladner et al. |
| 5,069,902 A | 12/1991 | Cook et al. |
| 5,143,825 A | 9/1992 | Chacko et al. |
| 5,208,023 A | 5/1993 | Nicholas et al. |
| 5,374,530 A | 12/1994 | Nuzzolo et al. |
| 5,498,551 A | 3/1996 | de Jaeger et al. |
| 5,750,113 A | 5/1998 | Cook |
| 5,846,527 A | 12/1998 | Miller et al. |
| 6,086,892 A | 7/2000 | Cook |
| 6,605,460 B1 * | 8/2003 | Goyal ........................ 435/236 |
| 2002/0192234 A1 * | 12/2002 | Goutebroze .............. 424/211.1 |

FOREIGN PATENT DOCUMENTS

| | | | |
|---|---|---|---|
| WO | WO 00/20600 | | 4/2000 |
| WO | WO 01/38497 A1 | * | 5/2001 |
| WO | WO 02/09576 | | 2/2002 |
| WO | WO 02/24147 | * | 3/2002 |

OTHER PUBLICATIONS

GenBank Accession No. AF072682.
GenBank Accession No. AF187154.
Ahmadian et al., "Detection and characterization of proteins encoded by the second ORF of the M2 gene of pneumoviruses," *J. Gen. Virol.*, 1999, 80:2011–2016.
Alexander, "Pneumovirus Infections (Turkey rhinotracheitis and Swollen Head Syndrome of Chickens)," *Diseases of Poultry*, 1991, pp. 669–673.
Alexander, *Diseases of Poultry*, 1997, Tenth Edition, Calnek et al. (eds.), Iowa State University Press, Ames, Iowa, pp. 541–569.

Ali and Reynolds "A Reverse Transcription–Polymerase Chain Reaction Assay for the Detection of Avian Pneumovirus (Colorado Strain)," *Avian Diseases*, 1999, 43:600–603.
Barnard et al., "Turkey Meningo–Encephalitis in South Africa," *Onderstepoort J. Vet. Res.*, 1980, 47(2):89–94.
Bartnicka and Minta, "Production of Monoclonal Antibodies Specific to Avian Pneumoviruses," *Bull. Vet. Inst. Pulawy*, 1997, 41:85–94.
Bennett et al., "Detection of Avian Pneumovirus in Wild Canada Geese (Branta canadensis) and Blue–Winged Teal (Anas discors)," *Avian Diseases*, 2002, 46:1025–1029.
Buraphacheep et al., "Detection of Antibodies to Respiratory Syncytial Virus Attachment and Nucleocapsid Proteins with Recombinant Baculovirus–Expressed Antigens," *J. Clin. Microbiol.*, 1997, 35(2):354–357.
Buys et al., "The Isolation and Attenuation of a Virus Causing Rhinotracheitis in Turkeys in South Africa," *Onderstepoort J. Vet. Res.*, 1989, 56:87–98.
Chettle and Wyeth, "Turkey Rhinotracheitis: Detection of Antibodies Using an ELISA Test," *Br. Vet. J.*, 1988, 144:282–287.
Chiang et al., "A modified enzyme–linked immunosorbent assay for the detection of avian pneumovirus antibodies," *J. Vet. Diagn. Invest.*, 2000, 12:381–384.
Coligan et al. (eds.), *Current Protocols in Immunology*, 1996, Greene Publishing Associates and Wiley–Interscience, John Wiley & Sons, New York, Chapters 2 and 8, pp. 2.0.1–2.11.12, 8.0.1–8.12.9.
Collins et al., "Antigenic differentiation of avian pneumovirus isolates using polyclonal antisera and mouse monoclonal antibodies," *Avian Pathology*, 1993, 22:469–479.
Cook et al., "A Live Attenuated Turkey Rhinotracheitis Virus Vaccine. 1. Stability of the Attenuated Strain," *Avian Pathology*, 1989, 18:511–522.
Cook et al., "Antigenic differentiation of strains of turkey rhinotracheitis virus using monoclonal antibodies," *Avian Pathology*, 1993, 22:257–273.
Cook et al., "Preliminary antigenic characterization of avian pneumovirus isolated from commercial turkeys in Colorado, USA," *Avian Pathology*, 1999, 28:607–617.
Cook, "Avian Pneumovirus Infections of Turkeys and Chickens," *Vet. J.*, 2000, 160:118–125.
Cortese et al., "Protection of pregnant cattle and their fetuses aginst infection with bovine viral diarrhea virus type 1 by use of a modified–live virus vaccine," *Am. J. Vet. Res.*, 1998, 59(11):1409–1413.

(Continued)

*Primary Examiner*—Ali R. Salimi
(74) *Attorney, Agent, or Firm*—Fish & Richardson P.C., P.A.

(57) ABSTRACT

Compositions and methods for ameliorating the clinical signs of an avian pneumovirus (APV) infection in a bird are disclosed. The compositions include immunologically effective amounts of an avirulent APV isolated from Canada geese. Methods for preparing avirulent Canada goose APV compositions and vaccines are also described.

18 Claims, 1 Drawing Sheet

OTHER PUBLICATIONS

Cote et al., "Generation of human monoclonal antibodies reactive with cellular antigens," *Proc. Natl. Acad. Sci. USA,* 1983, 80:2026–2030.

Dar et al., "PCR–Based Detection of an Emerging Avian Pneumovirus," *41st Annual Meeting, American Association of Veterinary Laboratory Diagnosticians,* Oct. 3–9, 1998, Minneapolis, MN, pg. 15, Abstract.

Drosten et al., "Evaluation of a new PCR assay with competitive internal control sequence for blood donor screening," *Transfusion,* 2000, 40:718–724.

Dubensky et al., "Live virus vaccines: Something old, something new, something borrowed. . . ," *Nature Medicine,* 1998, 4(12):1357–1358.

Elliott et al., "Nucleotide sequence of the matrix, fusion and putative SH protein genes of mumps virus and their deduced amino acid sequences," *Virus Research,* 1989, 12:61–75.

Eterradossi et al., "Evaluation of Different Turkey Rhinotracheitis Viruses used as Antigens for Serological Testing following Live Vaccination and Challenge," *J. Vet. Med. B,* 1995, 42:175–186.

Eterradossi et al., "Discrepancies in turkey rhinotracheitis ELISA results using different antigens," *Vet. Rec.,* 1992, 131:563–564.

Evan et al., "Isolation of Monoclonal Antibodies Specific for Human c–*myc* Proto–Oncogene Product," *Mol. Cell. Biol.,* 1985, 5(12):3610–3616.

Foley and Rosen, "Risks and benefits of modified–live versus killed virus vaccines in multiple–cat situations," *J. Am. Vet. Med. Assoc.,* 1999, 214(5):620, 622.

Gillette, "Enzyme–linked immunosorbent assay for serum antibody to bovine respiratory syncytial virus: Comparison with complement–fixation and neutralization tests," *Am. J. Vet. Res.,* 1983, 44(12):2251–2255.

Gough et al., "Experimental infection of turkeys, chickens, ducks, geese, guinea fowl, pheasants and pigeons with turkey rhinotracheitis virus," *Vet. Rec.,* 123:58–59.

Gough et al., "Isolation and identification of avian pneumovirus from pheasants," *Vet. Rec.,* 2001, 149:312.

Goyal et al., "Avian Pneumovirus ELISA: Determining Antibody Titers from a Single Serum Dilution," *Gobbles,* 2000, 56(12):19.

Goyal et al., "Isolation of avian pneumovirus from an outbreak of respiratory illness in Minnesota turkeys,"*J. Vet. Diagn. Invest.,* 2000, 12:166–168.

Grant et al., "An enzyme–lined immunosorbent assay for the serodiagnosis of turkey rhinotracheitis infection," *Vet. Rec.,* 1987, 120:279–280.

Gulati et al., "Development of a Highly Sensitive and Specific Enzyme–Linked Immunosorbent Assay Based on Recombinant Matrix Protein for Detection of Avian Pneumovirus Antibodies," *J. Clin. Microbiol.,* 2000, 38(11):4010–4014.

Gulati et al., "Protective Efficacy of High–Passage Avian Pneumovirus (APV/MN/turkey/1–a/97) in Turkeys," *Avian Diseases,* 2001, 45:593–597.

Harlow et al., *Antibodies: A Laboratory Manual,* 1988, Cold Spring Harbor Laboratory, p. 560.

Heckert et al., "Absence of antibodies to avian pneumovirus in Canadian poultry," *Vet. Rec.,* 1993, 132(7):172.

Heckert et al., "Development and Evaluation of an Enzyme–linked Immunosorbent Assay for the Detection of Antibodies to Avian Pneumovirus," *Avian Diseases,* 1994, 38:694–700.

Higgins, "Chapter 9—Comparative immunology of avian species," *Comparative Avian Immunology,* 1996, 24:149–205.

Hossain et al., "Egg–adapted replication–restricted virus protects mice against lethal influenza," *Vaccine,* 2000, 18:3082–3090.

Huse et al., "Generation of a Large Combinatorial Library of the Immunoglobulin Repertoire in Phage Lambda," *Science,* 1989, 246:1275–1281.

Jing et al., "Detection of turkey rhinotracheitis virus in turkeys using the polymerase chain reaction," *Avian Pathology,* 1993, 22:771–783.

Jirjis et al., "Avian Pneumovirus Infection in Minnesota Turkeys: Experimental Reproduction of the Disease," *Avian Diseases,* 2000, 44:222–226.

Jirjis et al., "Rapid detection of avian pneumovirus in tissue culture by microindirect immunofluorescence test," *J. Vet. Diagn. Invest.,* 2002, 14:172–175.

Jones, "Avian pneumovirus infection: questions still unanswered," *Avian Pathology,* 1996, 25:639–648.

Juhasz and Easton, "Estensive sequence variation in the attachment (G) protein gene of avian pneumovirus: evidence for two distinct subgroups," *J. Gen. Virol.,* 1994, 75:2873–2880.

Kelleher et al., "Isolation of Avian Paramyxoviruses from Sentinel Ducks and Turkeys in Minnesota," *Avian Diseases,* 1984, 29(2):400–407.

Kleven, *Proc. U.S. Animal Health Assoc. 101st Annual Meeting,* 1997, pp. 486–491.

Köhler and Milstein, "Continuous cultures of fused cells secreting antibody of predefined specificity," *Nature,* 1975, 256:495–497.

Kolodziej and Young, "Epitope Tagging and Protein Surveillance," *Methods in Enzymology,* 1991, 194:508–519.

Kozbor and Roder, "The production of monoclonal antibodies form human lymphocytes," *Immunology Today,* 1983, 4(3):72–79.

Kowk and Higuchi, "Avoiding false positives with PCR," *Nature,* 1989, 339:237–238.

Li et al., "Sequence of the nucleocapsid protein gene of subgroup A and B avina pneumoviruses," *Virus Res.,* 1996:41:185–191.

Lister and Alexander, "Turkey Rhinotracheitis: A Review," *Vet. Bull.,* 1986, 56(8):637–663.

Maharaj et al., "Isolation of an avian pneumovirus–like agent from broiler breeder chickens in South Africa," *Vet. Rec.,* 1994, 134(20):525–526.

Mavromatis et al., "Field Evaluation of a Live Vaccine against Porcine Reproductive and Respiratory Syndrome in Fattening Pigs," *J. Vet. Med. B,* 1999, 46:603–612.

Muir and Kent, "The chemical synthesis of proteins," *Curr. Opin. Biotechnol.,* 1993, 4:420–427.

Naylor and Jones, "Turkey rhinotracheitis: a review," *Vet. Bull.,* 1993, 63(5):439–449.

O'Loan et al., "An improved ELISA and serum neutralisation test for the detection of turkey rhinotracheitis virus antibodies," *J. Virological Meth.,* 1989, 25:271–282.

Par'e et al., "Humoral Resposne and Protection from Experimental Challenge Following Vaccination of Raccoon Pups with a Modified–Live Canine Distemper Virus Vaccine," *J. Wildlife Diseases,* 1999, 35(3):430–439.

Pastey and Samal, "Baculovirus Expression of the Fusion Protein Gene of Bovine Respiratory Syncytial Virus and Utility of the Recombinant Protein in a Diagnostic Enzyme Immunoassay," *J. Clin. Microbiol.,* 1998, 36(4):1105–1108.

Pattison, "TRT in the Field: Field Situation and Control," *Proceedings & Technical Supplement of the Roche Avian Pneumovirus Workshop,* Clark et al. (eds.), 1998, Parsoppany, NJ, RCD 9713, pp. 43–49.

Pratelli et al., "Immunization of Pups with Maternally Derived Antibodies to Canine Parvovirus (CPV) Using a Modified–Live Variant (CPV–2b)," *J. Vet. Med. B,* 2000, 47:273–276.

Prevel, "Differentiation of avian pneumovirus isolates by monoclonal antibodies to detect turkey rhinotracheitis antibodies in ELISA," Thesis, 1995, Tierarztliche Hochschule (publ.), Hannover, Germany, 1 pg., (Abstract only).

Pringle, "Chapter 5—Pneumoviruses," *Virology: A Practical Approach,* 1985, Mahy (ed.), IRL Press, Oxford, pp. 95–117.

Pringle, "Virus Taxonomy 1996—A bulletin from the Xth International Congress of Virology in Jerusalem," *Arch. Virol.,* 1996, 141:2251–2256.

Randhawa et al., "Nucleotide Sequence of the Matrix Protein Gene of a Subgroup B Avian Pneumovirus," *Virus Genes,* 1996, 12(2):179–183.

Randhawa et al., "Rescue of Synthetic Minireplicons Establishes the Absence of the NS1 and NS2 Genes from Avian Pneumorivus," *J. Virol.,* 1997, 71(12):9849–9854.

Reed and Muench, "A Simple Method of Estimating Fifty Per Cent Endpoints," *Am. J. Hygiene,* 1938, 27(3):493–497.

Roy et al., "Efficacy of live adjuvanted mesogenic Newcastle disease vaccine in chickens," *Vaccine,* 1999, 17:2764–2676.

Samal et al., "Reliable Confirmation of Antibodies to Bovine Respiratory Syncytial Virus (BRSV) by Enzyme–Linked Immunosorbent Assay Using BRSV Nucleocapsid Protein Expressed in Insect Cells," *J. Clin. Microbiol.,* 1993, 31(12):3147–3152.

Seal, "Analysis of Matrix Protein Gene Nucleotide Sequence Diversity Among Newcastle Disease Virus Isolates Demonstrates that Recent Disease Outbreaks Are Caused by Viruses of Psittacine Origin," *Virus Genes,* 1996, 11(2/3):217–224.

Seal, "Matrix protein gene nucleotide and predicted amino acid sequence demonstrate that the first US avian pneumovirus isolate is distinct from European strains," *Virus Res.,* 1998, 58:45–52.

Seal, "Avian pneumoviruses and emergence of a new type in the United States of America," *Animal Health Research Reviews,* 2000, 1(1):67–72.

Seal et al., "Fusion protein predicted amino acid sequence of the first US avian pneumovirus isolate and lack of heterogeneity among other US isolates," *Virus Res.,* 2000, 66:139–147.

Shin et al., "Specific detection of avian pneumovirus (APV) US isolates by RT–PCR," *Arch. Virol.,* 2000, 145:1239–1246.

Shin et al., "Avian Pneumovirus (APV) RNA from Wild and Sentinel Birds in the United States Has Genetic Homology with RNA from APV Isolates from Domestic Turkeys," *J. Clin. Microbiol.,* 2000, 38(11):4282–4284.

Shin et al., "Susceptibility of ducks to avian pneumovirus of turkey origin," *Am. J. Vet. Res.,* 2001, 62(7):991–994.

Shin et al., "Isolation of avian pneumovirus from mallard ducks that is genetically similar to viruses isolated form neighboring commerical turkeys," *Virus Res.,* 2002, 83:207–212.

Smith et al., "Fluorescence detection in automated DNA sequence analysis," *Nature,* 1986, 321:674–681.

Sowa et al., "Zur humoralen Immunantwort beim Huhn nach Vakzinierung gegen Rhinotracheitis der Puten," *Arch. Geflügelk.,* 1999, 64(2):55–60, (includes English summary).

State of Minnesota, *Board of Animal Health,* Annual Report, Jul. 1, 1998—Jun. 30, 1999, 1 pg.

State of Minnesota, *Board of Animal Health,* Annual Report, Jul. 1, 1999—Jun. 30, 2000, 1 pg.

Tanaka et al., "A Serological Survey of Turkey Rhinotracheitis Virus Infection in Chickens in Japan," *J. Vet. Med. Sci.,* 1996, 58(7):689–691.

Towbin et al., "Electrophoretic transfer of proteins from polyacrylamide gels to nitrocellulose sheets: Procedure and some applications," *Proc. Natl. Acad. Sci. USA,* 1979, 76(9):4350–4354.

West et al., "The efficacy of modified–live bovine respiratory syncytial virus vaccines in experimentally infected calves," *Vaccine,* 2000, 18:907–919.

Williams et al., "Further studies on the development of a live attenuated vaccine against turkey rhinotracheitis," *Avian Pathology,* 119, 20:585–596.

Yu et al., "Sequence and in vitro expression of the M2 gene of turkey rhinotracheitis pneumovirus," *J. Gen. Virol.,* 1992, 73:1355–1363.

Yu et al., "Cloning and Sequencing of the Matrix Protein (M) Gene of Turkey Rhinotracheitis Virus Reveal a Gene Order Different from That of Respiratory Syncytial Virus," *Virology,* 1992, 186:426–434.

* cited by examiner ggtcaatgcatcagcacaaggggctgcaatgtcagcattgccaaaaagctttgatgttagtgcatcagtag
cactagatgaccacagcaaactagagtttgacaaactgacagtgtgtgagttaaaagcagtctatttgaca
acaatgaaaccttatggtatggtctcaaagtttgtcaactcagccaaagcagtcgggaagaaaaccccg
atttgattgctctctggggcttccttgacctagagaagggagttccagtgactataccagcctatataaagtc
tgtgtcaataaaagagagtgaatcagcaactgttgaggctgcaattagtggggaggcagatcaagctata
actcaagctaggattgctccatacgctggcttgatcatgataatgacaatgaacaaccctaaggggatcttc
aaaaaactgggtgcaggagttca (SEQ ID NO:3)

Figure 1

SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide

<400> SEQUENCE: 1
ggtcaatgca tcagcacaag        20

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide

<400> SEQUENCE: 2
tgaactcctg cacccagttt        20

<210> SEQ ID NO 3
<211> LENGTH: 450
<212> TYPE: DNA
<213> ORGANISM: Artificial Sequence
<220> FEATURE:
<223> OTHER INFORMATION: M gene amplification product

<400> SEQUENCE: 3
ggtcaatgca tcagcacaag gggctgcaat gtcagcattg ccaaaaagct ttgatgttag        60
tgcatcagta gcactagatg accacagcaa actagagttt gacaaactga cagtgtgtga       120
gttaaaagca gtctatttga caacaatgaa acctatggt atggtctcaa agtttgtcaa       180
ctcagccaaa gcagtcggga agaaaacccc cgatttgatt gctctctggg gcttccttga       240

```
cctagagaag ggagttccag tgactatacc agcctatata aagtctgtgt caataaaaga    300
gagtgaatca gcaactgttg aggctgcaat tagtggggag gcagatcaag ctataactca    360
agctaggatt gctccatacg ctggcttgat catgataatg acaatgaaca accctaaggg    420
gatcttcaaa aaactgggtg caggagttca                                     450
```

AVIAN PNEUMOVIRUS VACCINE

TECHNICAL FIELD

This invention relates to avian vaccines, and more particularly to avian pneumovirus vaccines.

BACKGROUND

Avian pneumovirus (APV) is a member of the Paramyxoviridae family of viruses. Pringle, 1996, *Arch. Virol.*, 141:2251–2256. It is the etiological agent of turkey rhinotracheitis (TRT), causing an acute upper respiratory tract infection characterized by coughing, nasal discharge, tracheal rales, foamy conjunctivitis and sinusitis in young poults. In laying birds, there is a transient drop in egg production along with mild respiratory tract illness. Jones, 1996, *Avian Pathol.*, 25:639–648. While uncomplicated cases of APV infection usually result in low mortality, secondary bacterial and/or viral infections can result in Lip to 25% mortality. Id.

APV was first detected in South Africa in 1978, and later detected in the UK, France, Spain, Germany, Italy, Netherlands, Israel, and Asia. See Alexander, 1997, In *Diseases of Poultry*; 10$^{th}$ Edition, Barnes et al., eds., 541–569; and Jones, supra. The first United States APV case was in Colorado in 1996. See Kleven, 1997, *Proc. U.S. Animal Health. Assoc.* 101$^{st}$ *Annual Mtg.*, 486–491. Subsequent APV infections were reported in Minnesota and neighboring states. See Lauer, 1999, *Minnesota Poultry Testing Laboratory Monthly Report*. By 1999, at least 37% of the turkey flocks in Minnesota were positive for APV antibodies, causing economic losses of approximately 15 million dollars per year.

APV virus has been detected in some wild bird species (see, for example, Shin et al., 2000, *J. Clin. Micro.*, 38:4282–4284), and other paramyxoviruses have been isolated from waterfowl (see, for example, Kelleher et al., 1984, *Avian Dis.*, 29:400–407). Experimental studies have shown that Peking ducks (*Anas platyrhynchos*) are susceptible to infection with APV (Shin et al., 2001, *Am. J. Vet. Res.*, 62:991–994). In addition, the virus has been detected in sentinel Mallard ducks (*Anas platyrhynchos*) (Shin et al., 2000, *J. Clin. Micro.*, 38:4282–4284). More recent studies have shown that sentinel Mallard ducks living in a pond adjacent to a turkey farm with an APV outbreak acquired the virus and developed anti-APV antibodies (Shin et al., 2002, *Virus Res.*, 83:207–212).

SUMMARY

In one aspect, the invention features an isolated avirulent Canada goose avian pneumovirus (aCg/APV). The invention also features a composition that includes an immunologically effective amount of an aCg/APV. In some embodiments, the composition further includes a pharmaceutically acceptable carrier. In other embodiments, aCg/APV isolates are designated APV/Canada goose/Minnesota/15a, APV/Canada goose/Minnesota/15b, APV/Canada goose/Minnesota/15c, APV/Canada goose/Minnesota/15d, and are assigned ATCC Accession Nos. PTA-4840, PTA-4841, PTA-4842, and PTA-4843, respectively.

These compositions containing an immunologically effective amount of an avirulent Canada geese APV are effective for lowering the risk of an APV infection in wild birds and domesticated birds. In particular, the compositions are useful for preventing an APV infection in poultry including turkeys, chickens, ducks, geese, pheasants, partridges, guinea fowl, and peacocks. In addition, the APV compositions are effective for ameliorating the clinical signs of an APV infection in a challenged bird.

In another aspect, the invention features methods for preparing an aCg/APV composition that includes the steps of providing a Canada goose APV (Cg/APV), and identifying avirulent Canada goose APV (aCg/APV) isolates. The Cg/APV can be cultured in and isolated from avian or non-avian cells, or a combination thereof. For example, the Cg/APV can be cultured in Vero cells, quail tumor cells (QT-35 cells) or chicken embryo fibroblasts (CEF). These methods result in the production of an aCg/APV that is effective for reducing or preventing the incidence of the clinical signs of an APV infection in poultry and, in particular, turkeys and chickens.

In another aspect, the invention features a method for reducing the risk of an APV infection in a bird by inoculating a bird with an immunologically effective amount of a composition including an aCg/APV. In some embodiments, the inoculated bird is allowed to become seropositive. Although many different dosages may be used to inoculate a bird, particularly useful dosages include at least $1.0 \times 10^1$ tissue culture infective dose (TCID$_{50}$) of an aCg/APV composition, at least $1.0 \times 10^2$ TCID$_{50}$ of an aCg/APV composition, at least $1.0 \times 10^3$ TCID$_{50}$ of an aCg/APV composition, at least $1.0 \times 10^5$ TCID$_{50}$ of an aCg/APV composition, or at least $1.0 \times 10^7$ TCID$_{50}$ of an aCg/APV composition.

Any method of inoculation can be used including applying the composition to one or more eyes of a bird and/or one or more nostrils of a bird, aerosolizing the vaccine into the turkeys' habitat, supplying an avirulent Canada geese APV composition in the drinking water of a bird, or injecting an avirulent Canada geese APV composition into a bird subcutaneously or intramuscularly. Inoculated birds can be representative members of a flock of birds and the inoculated or vaccinated birds can cause a majority of the flock to become seropositive. Alternatively, all birds can be vaccinated simultaneously be aerosolization, by placing the vaccine in drinking water, or by instilling the vaccine in the eye and/or nostril of all birds. In some embodiments, the method is effective for reducing the incidence of the clinical signs of an APV infection in a challenged bird.

In another aspect, the invention features an inoculated bird, which is a bird containing an inoculant of an immunologically effective amount of an aCg/APV. In some embodiments, the bird is allowed to become or is seropositive for APV. In another aspect, the invention features a body part, such as a meat portion, of an inoculated or vaccinated bird. In particular, these birds can be turkeys.

In yet another aspect, the invention features compositions containing immunologically effective amounts of an aCg/APV that has been inactivated. In some embodiments, the composition further includes a pharmaceutically acceptable carrier or adjuvant. Compositions containing an inactivated, aCg/APV are also effective for lowering the risk of an APV infection in poultry, such as chickens or turkeys, and in other domesticated and wild birds. The compositions are also effective for ameliorating the clinical signs of an APV infection in a challenged bird. In some embodiments, inactivation is by formalin or β-propiolactone inactivation.

In another aspect, the invention features an article of manufacture containing an aCg/APV composition. The composition can be combined with packaging materials and instructions for their use. The instructions can describe how an aCg/APV vaccine is effective for preventing the incidence of an APV infection, preventing the occurrence of the clinical signs of an APV infection, ameliorating the clinical signs of an APV infection, lowering the risk of the clinical signs of an APV infection, lowering the occurrence of the clinical signs of an APV infection and/or lowering the spread of APV infections in birds. The articles of manufacture may combine one or more aCg/APV vaccines.

Articles of manufacture can also include diagnostic molecules (e.g., antibodies, indicator molecules, and/or other useful agents) that are effective for detecting the presence of APV or other avian infections in birds. Moreover, it is to be understood that aCg/APV vaccines themselves and/or articles of manufacture that include aCg/APV vaccines can include other components conventional to the art, for example sterile water, pharmaceutical carriers, vaccine carriers, and buffers that are useful for maintaining the viability of the APV vaccines. Conveniently, the aCg/APV vaccines of the invention may be provided in a pre-packaged form in quantities sufficient for a protective dose for a single bird or for a pre-specified number of birds in, for example, sealed ampoules, capsules or cartridges. The APV vaccines and/or articles of manufacture may also contain other virus strains, microorganisms, and antigens that protect the inoculated birds against other avian diseases.

It is to be further understood that each of the embodiments may be combined with any of the other embodiments described herein. For example, the methods disclosed herein are useful with any of the compositions, or articles of manufacture, and the dosages may be used in any of the various embodiments described herein.

Advantages of the invention include a safe and effective way to protect birds, especially turkeys, from an APV infection. Moreover, the invention can provide methods for raising antibodies to APV to be used in diagnostic kits and may be used in the diagnostic kits for detecting the presence of APV.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DESCRIPTION OF DRAWINGS

Like reference symbols in the various drawings indicate like elements.

DETAILED DESCRIPTION

The invention features avirulent APV isolates obtained from Canada geese (aCg/APV), compositions containing one or more aCg/APVs, and methods for preparing an aCg/APV. An avian composition (e.g., a vaccine) can contain an immunologically effective dosage of an aCg/APV. These aCg/APV vaccines are both safe and immunogenic when administered to birds. Vaccinated birds are seropositive for anti-APV antibodies and resistant to infection by or challenge with a virulent APV. Using the compositions and/or vaccines described herein is an effective way for preventing, ameliorating, lowering the risk of, lowering the occurrence of and/or spread of APV infections in birds.

AcG APV Compositions and Their Uses

APV compositions of the invention contain an aCg/APV. A composition of the invention can be formulated in an immunologically effective dose and used, for example, as a vaccine. Vaccines of the invention are useful for any type of bird susceptible to APV infection including domesticated and wild birds. In particular, the vaccines described herein are useful for inoculating and/or treating birds living in flocks or other types of close living arrangements where an APV infection can rapidly spread from bird to bird. Domesticated birds that may benefit from receiving an aCg/APV vaccine include poultry such as turkeys, chickens, ducks, geese, pheasants, partridges, guinea fowl, peacocks, and any other type of domesticated bird. Wild birds that may benefit from receiving an aCg/APV vaccine include starlings, sparrows, turkeys, ducks, geese, pheasants, partridges, guinea fowl, peacocks, and any other type of wild bird that may contract an APV infection and/or transmit APV infection to another bird.

An immunologically effective dosage of an aCg/APV vaccine is a dosage that, when administered to a bird, elicits an immunological response in the bird but causes the bird to develop mild or no clinical signs of an APV infection. A bird that has received an immunologically effective dosage is an inoculated bird or a bird containing an inoculant of an immunologically effective amount of an aCg/APV. When an immunological response is produced in the bird, the bird is considered seropositive, i.e., the bird produces a detectable amount of anti-APV antibodies. Methods for detecting an immunological response in a bird are known, e.g., Chiang et al., 2000, *J. Vet. Diag. Invest.*, 12:381–84.

Mild clinical signs can include watery eyes, nasal discharge or cough in a flock from about 5 to about 12 days post inoculation ("dpi"). The clinical signs of APV and other upper respiratory infections in birds are known. The clinical signs of an APV infection in turkeys include profuse ocular and nasal discharge, watery eyes, unilateral or bilateral sinus swelling, facial edema or swelling, depression, coughing, sinusitis, airsacculitis, respiratory distress, and mortality. In laying turkeys, a drop in egg production associated with respiratory distress may be seen.

As used herein, a vaccinated bird is an inoculated bird that is seropositive. Vaccinated birds can exhibit an immunological response following a challenge with a virulent APV. A vaccinated bird is resistant to or immune to an APV infection if it fails to develop clinical signs of APV infection or develops mild signs of APV infection after being challenged with a virulent APV. As a result, vaccinated birds that are subsequently challenged with a virulent APV may still pass slaughter inspections and continue to market. Methods and rating systems for passing or condemning birds destined for slaughter are known.

A vaccinated bird may shed the aCg/APV. Shedding is typically detectable from about 5 days to about 7 days post inoculation, and may range from 3 days to 21 days post inoculation. Methods for detecting the shedding of an APV are known. Useful methods include the methods described in Shin et al., 2000, *Arch. Virol.*, 145:1239–46; and Goyal et al., 2000, *J. Vet. Diagn. Invest.*, 12:166–68.

Virulent APV isolates are those isolates that cause a bird to develop clinical signs of an APV infection, to be unfit for market, and/or to die, provided the bird has not been previously exposed to APV and/or an APV vaccine. An APV isolate is virulent if it causes clinical signs of an APV infection in a bird at a dosage of at least $1.0 \times 10^2$ tissue culture infective dose ($TCID_{50}$). Avirulent APV isolates are those APV isolates that cause mild or no clinical signs of an APV infection in a bird at a dosage of about $1.0 \times 10^2$ $TCID_{50}$.

Methods for determining virus titers and $TCID_{50}$ are known. The $TCID_{50}$ is the reciprocal of the highest dilution of a virus that causes a specified reaction in 50% of the host cells inoculated with, or exposed to, that particular dilution of virus. Oftentimes with pathogenic viruses, the specified reaction is cytopathic effects such as cell rounding. See, e.g., Cook et al., 1989, *Avian Pathology*, 18:511–522.

Immunologically effective dosages can be determined experimentally and may vary according to the type, size, age, and health of the bird vaccinated. For example, an immunologically effective amount for a two-week-old turkey poult may include an APV vaccine dosage of about 200 µL of a $1.0 \times 10^1$ $TCID_{50}$/ml stock vaccine solution. Older turkeys may require larger dosages. For example, a dosage of at least about 200 µl of a $1.0 \times 10^3$ $TCID_{50}$/bird stock vaccine solution can be administered to a bird, and doses as high as 200 µl of a $1.0 \times 10^5$ $TCID_{50}$/bird or a $1.0 \times 10^7$ $TCID_{50}$/bird stock vaccine solution can be administered. Dosages smaller than 200 µl of a $1.0 \times 10^1$ $TCID_{50}$/bird stock solution may result in ineffective vaccinations, and dosages larger than 200 µl of a $1.0 \times 10^7$ $TCID_{50}$/bird stock vaccine solution may be less cost effective. The vaccination may include a single inoculation or multiple inoculations. Other dosage schedules and amounts including vaccine booster dosages may be useful.

The age of the bird receiving a vaccination may depend upon the type of bird and the purpose for which the bird is being kept. For example, it may be preferable to inoculate meat-producing birds in ovo, or at a young age, perhaps as newborns or hatchlings or when the birds are only a few weeks old. Alternatively, it may be useful to vaccinate egg-producing birds at other times, e.g., shortly before they are about to lay (perhaps with a vaccine booster dosage) so that maternal antibodies may be transmitted to the young. Of course, it may also be useful to inoculate egg-laying birds at an early age to prevent APV infection in the egg-laying flock.

The immunologically effective dosage of an aCg/APV composition may be given to a bird using any known method for inoculating birds including direct application intranasally or intraocularly, aerosolizing into a birds habitat, administering via a birds' water supply, and/or injecting subcutaneously or intramuscularly. The inoculation can be given to a single nostril or eye or divided between one or more nostrils/eyes. For example, a 200 µl dosage containing $1.0 \times 10^2$ $TCID_{50}$/ml can be evenly divided into four 50 µl dosages and administered to both nostrils and both eyes of a bird.

Alternatively, an immunologically effective dosage may be given to each member of a flock directly or the dosage can be applied to the food and/or water supply of a flock. For example, an immunologically effective dosage of an aCg/APV, e.g., about $1.0 \times 10^3$ $TCID_{50}$/bird, can be aerosolized into the birds' habitat. Alternatively, an immunologically effective dosage can be dissolved in the water supply of a flock of birds. Most, if not all, of a flock should become vaccinated birds at approximately the same time when inoculating the flock through the food, water, or air supply. Dosages administered through the food or water supply can be easily computed by multiplying the amount a single bird eats or drinks per day by the number of birds to be inoculated to compute the unit of food or water consumed per day per bird. Then, the unit of food or water consumed per day is used to compute the vaccine dosage needed to dissolve in that unit of food or water so as to deliver, for example, at least $1.0 \times 10^2$ $TCID_{50}$/bird.

aCg/APV compositions or vaccines that are inactivated can be used in the same manner and under the same conditions used for aCg/APV compositions that are not inactivated. Inactivated APV vaccines are useful for any type of bird susceptible to APV infection including domesticated and wild birds. Methods for making inactivated virus vaccines are well known and include the use of formalin or β-propiolactone to make inactivated vaccines. Inactivated APV compositions or vaccines are typically administered by subcutaneous or intramuscular injection because they are no longer living. Such compositions may further include an adjuvant and/or pharmaceutical carrier.

Compositions containing an aCg/APV also have uses other than as a vaccine. These compositions may be used to induce a bird to raise antibodies to APV to be used in diagnostic tests for identifying one or more APV isolates. Further, the aCg/APV may be used in a diagnostic assay for detecting the presence of anti-APV antibodies in the sera of a bird. Methods for raising and purifying antibodies are known. Methods for preparing diagnostic kits for detecting antibodies in a serum source are known.

Methods for Obtaining Avirulent Canada Geese APV

An aCg/APV can be obtained by culturing APV from Canada geese in host cells, and determining the virulence of the Canada goose (Cg) APV. Methods for obtaining Canada geese APV first include the step of obtaining specimens from Cg. Specimens can be obtained using tracheal swabs, turbinates, or by isolating the trachea and/or lungs. Such birds may or may not be exhibiting clinical signs of an APV infection. The specimens are then used to inoculate hosts such as embryonated chicken eggs ("ECE"), embryonated turkey eggs ("ETE") or chicken embryo fibroblasts (CEF). APV can be isolated using any known method for isolating avian viruses. The methods described in Goyal et al., 2000, *J. Vet. Diagn. Invest.*, 12:166–68 provide illustrative methods for isolating a turkey APV, and can be adapted for other avian viruses.

Subsequently, the APV can be grown in host cells such as CEF, quail tumor cell lines, Vero cells, or other avian or non-avian cells using known methods (see, for example, Pringle, In *Virology: A Practical Approach*, pp 95–117, IRL Press, Oxford, Washington, D.C.). A single type of cell or multiple types of cells can be used to isolate, identify, passage, and titrate APV. See Naylor et al., 1993, *Vet. Bull.*, 63:439–49. Useful quail tumor cell lines include QT-35. Useful Vero cells include those available from the American Type Culture Collection (ATCC, 10801 University Blvd., Manassas, Va. 20110) having the designation CCL81. The infected host cells are incubated and passaged under standard conditions. It may be necessary for the infected host cells to undergo one or more blind passages before cytopathic effects, such as cell rounding, are observed. Cytopathic effects produced by various viruses in various cell cultures are well known. If no cytopathic effects are observed, the presence of the virus can be confirmed using, for example, PCR or immunofluorescence assays.

Host cells can be inoculated with a virus using any known method. To isolate virus particles from cells, the cells can be subjected to repeated freezing and thawing, or the cells can be sonicated. Cellular debris is removed by centrifugation and the supernatant containing virus particles then can be used to inoculate a different host cell. Although the length of each passage in a particular host cell may vary, each passage is typically 4–5 days in length. An aCg/APV is isolated when it has been removed from its original host, passaged in cell culture, and removed from the cells. The presence of a virus in cell culture can be confirmed using any known method. The presence of APV following isolation can be confirmed using RT-PCR as described in Dar et al., 1998, *Proc. Annual Meeting Am. Assoc. Vet. Lab. Diagn.*, 41:18. Following removal from cell culture, a dosage of at least $1.0 \times 10^2$ $TCID_{50}$ of the aCg/APV can be administered to a bird that has not been exposed to APV and produces mild or no clinical signs of an APV infection in the bird.

Alternatively, APV may be directly isolated from an inoculation specimen using CEF, quail tumor cells, Vero cells, or other avian or non-avian cells. Briefly, tracheal swabs can be used to directly inoculate monolayers of, for example, CEF, quail tumor cells, or Vero cells. The host cells are passaged generally until cytopathic effects are observed and the virus isolated from cells by freezing and thawing.

Useful aCg/APV compositions were deposited with the ATCC on Dec. 4, 2002 and received ATCC Accession Nos. PTA-4840, PTA-4841, PTA-4842, and PTA-4843. In addition to the methods described herein, an aCg/APV composition or vaccine of the invention can be produced using any known method for producing viral compositions and vaccines. See, e.g., Williams et al., *Avian Pathology*, 20:585096 (1991). An aCg/APV vaccine of the invention is a vaccine that is safe, immunogenic, and avirulent in turkeys.

Article of Manufacture Containing APV Vaccines

A virulent Canada geese APV compositions or vaccines as described herein can be combined with packaging materials including instructions for their use to be sold as articles of manufacture or kits. Components and methods for producing articles of manufacture are well known. Instructions describing how an avirulent Canada geese APV vaccine is effective for preventing the incidence of an APV infection, preventing the occurrence of the clinical signs of an APV infection, ameliorating the clinical signs of an APV infection, lowering the risk of the clinical signs of an APV infection, lowering the occurrence of the clinical signs of an APV infection and/or spread of APV infections in birds may be included in such kits. The articles of manufacture may combine one or more avirulent Canada geese APV vaccines as described herein. In addition, the article of manufacture can also include diagnostic molecules (e.g., antibodies, indicator molecules, and/or other useful agents) that are effective for detecting the presence of APV or other avian infections in birds.

It is to be understood that avirulent Canada geese APV vaccines themselves and/or articles of manufacture that include a virulent Canada geese APV vaccines can include other components conventional to the art, for example sterile water, pharmaceutical carriers, vaccine carriers, and buffers that are useful for maintaining the viability of the APV vaccines. The APV vaccines and/or articles of manufacture may also contain other virus strains, microorganisms, and antigens that protect the inoculated birds against other avian diseases. Methods for producing such multi-effect vaccines are known. Conveniently, the a virulent Canada geese APV vaccines may be provided in a pre-packaged form in quantities sufficient for a protective dose for a single bird or for a pre-specified number of birds in, for example, sealed ampoules, capsules or cartridges. Avirulent Canada geese APV vaccines may also be supplied in a freeze-dried form.

Avirulent Canada geese APV vaccines may be combined with different vaccines or preventative methods directed to other avian diseases so as to produce birds that are relatively pathogen free, healthier, and/or resistant to more avian diseases than just APV. Other avian diseases include *Ornithobacterium rhinotracheale, Bordetella avium,* avian influenza, New Castle Disease, *Mycoplasma* spp., and *Pasteurella multocida*.

The invention will be further described in the following examples, which do not limit the scope of the invention described in the claims.

EXAMPLES

Example 1

Sampling

The University of Minnesota College of Natural Resources and Minnesota Department of Natural Resources conducted an annual Canada goose (*Branta canadensis*) roundup to remove nuisance geese from the Minneapolis/St. Paul metropolitan area during the period when the adult birds were molting and before the juveniles (the current year's hatchlings) were fledged. These geese were located at least 25 miles from any domestic turkey farm and at least 50 miles from APV-positive turkey farms. The geese were captured and transferred to holding pens. Sampling was conducted as the geese were loaded from the holding pens onto transport trucks. In 2000, choanal cleft swab samples were collected from 95 juvenile and 175 adult Canada geese. In 2001, choanal cleft swabs were collected from 400 juvenile and 100 adult Canada geese.

Waterfowl in Stutsman County, N.Dak. were captured and banded during the month of August as part of the Central Flyway Banding Project conducted by the Central Flyway Council. In 2000, choanal cleft swabs were collected from 110 adult Blue-winged teal (*Anas discors*) and 45 juvenile Blue-winged teal. In 2001, choanal cleft swabs were collected from 180 juvenile Blue-winged teal and 23 adult Blue-winged teal.

Example 2

Sample Handling

All samples were transported in minimal essential medium (MEM) (Gibco, Grand Island, N.Y.) containing 200 units/ml penicillin G sodium, 200 $\mu$g/ml streptomycin sulfate, 0.75 $\mu$g/ml amphotericin B, and 150 $\mu$g/ml gentamicin. In 2000, five samples were pooled per tube and first screened for APV by Taqman reverse transcription polymerase chain reaction (RT-PCR) prior to inoculation onto tissue culture (samples were frozen at −70° C. until the results were known). All teal APV positive samples and the ten APV positive goose samples with the highest reading according to the quantitative Taqman RT-PCR samples were selected for virus isolation.

In 2001, ten samples were pooled per tube. All goose samples were inoculated onto tissue culture or into specific pathogen-free (SPF) eggs (Charles River SPAFAS, North Franklin, Conn.) immediately after arrival at the laboratory, but only samples that were APV positive by RT-PCR were continued for further passages. In 2001, the teal samples were frozen for transport to the laboratory and inoculated onto chicken embryo fibroblasts (CEF) and into SPF eggs upon arrival at the laboratory.

Example 3

5'-Nuclease APV RT-PCR

A TaqMan RT-PCR for APV developed by the University of Minnesota Diagnostic Laboratory (Drosten et al., 2000, *Transfusion*, 40:718–724; Kwok & Higuchi, 1989, *Nature*, 339:237–238) was used to confirm APV. The procedure detects nucleic acid sequences from the matrix (M) gene and the primers were designed in such a way that it is capable of detecting all APV strains in the United States (i.e., subtypes C). The one-tube detection of APV RNA with a fluorogenic probe, using 5'-nuclease RT-PCR technology (TaqMan® PCR) eliminated the risk of carryover contamination, a major problem in PCR testing.

TaqMan® PCR resulted in a 424 basepair fragment of the APV M gene. The TaqMan® PCR was performed in a volume of 25 µl containing a mixture of Omniscript and Sensicript reverse transciptases (QIAGEN, Valencia, Calif.) and HotStarTaq DNA polymerase, RNAse inhibitor, and M gene forward and reverse primers. The APV M gene primers had the following sequences: 5'-GGT CAA TGC ATC AGC ACA AG-3' (forward) (SEQ ID NO:1) and 5'-TGA ACT CCT GCA CCC AGT TT-3' (reverse) (SEQ ID NO:2). The primers were used at a concentration of approximately 500 nM each.

Figure 1:
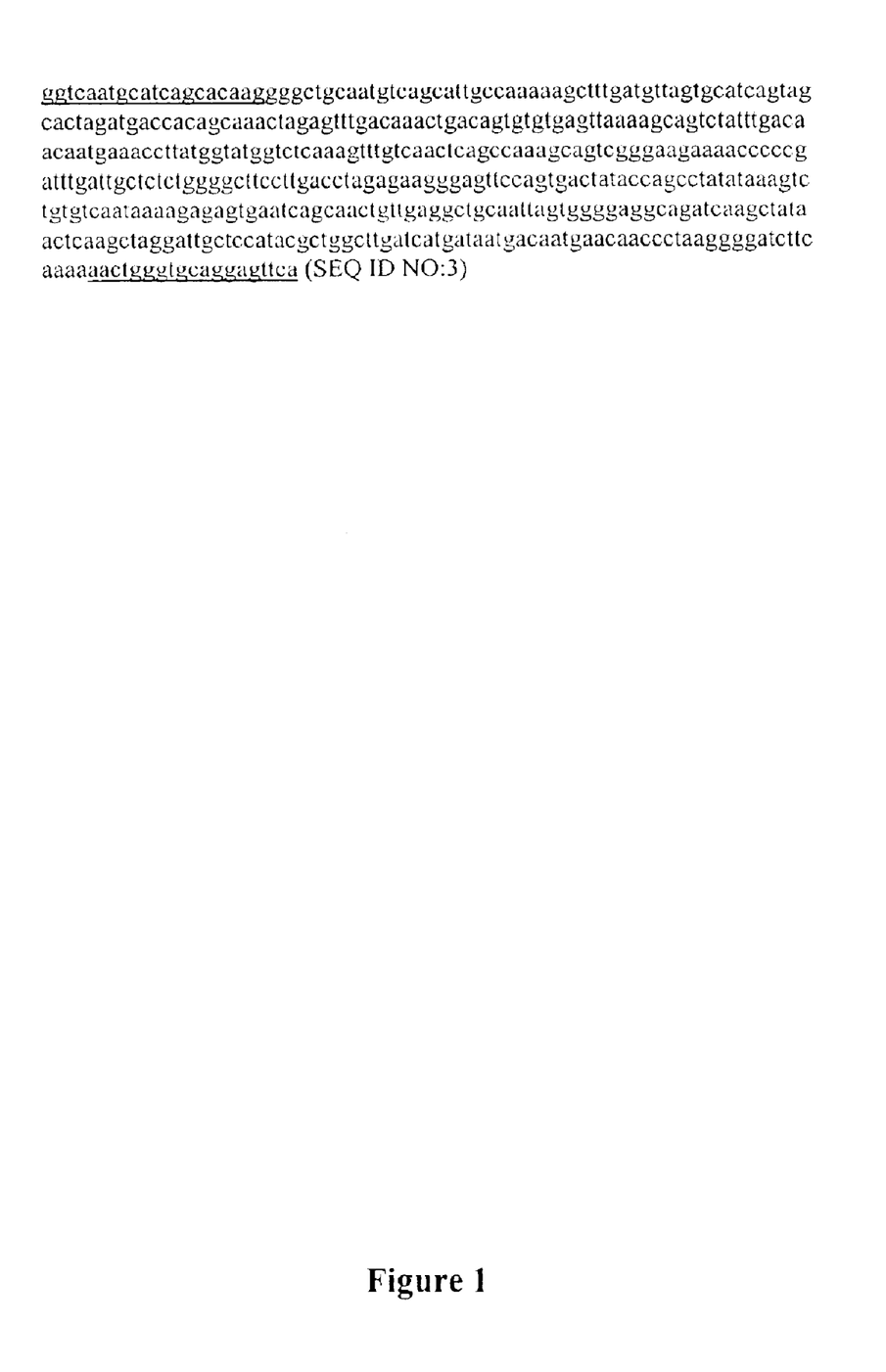
FIG. 1 shows the sequence of the M gene amplification product (SEQ ID NO:3) generated by TaqMan® PCR as described in Example 3.

An APV M gene probe was labeled at the 5' end with 6-carboxyfluorescein (FAM) as the reporter and at its 3' end with 6-carboxy-tetramethylrhodamine (TAMRA) as the quencher. The APV M gene probe was cleaved by 5' nuclease activity of Taq DNA polymerase only if the target sequence was amplified. A reaction was considered positive for APV sequences when there was a signal from the FAM emission wavelength (518 nm), negative when there was a signal from the TAMRA emission wavelength only, and non-valid when there was no signal (Drosten et al., 2000, *Transfusion*, 40:718–724; Kwok & Higuchi, 1989, *Nature*, 339:237–238). The sequence of the probe used in these experiments is proprietary. A probe suitable for use in the invention, however, can be designed to hybridize to the amplification product at any position along its length. The amplification product that was generated using the above-indicated APV M gene primers is shown in FIG. 1 (SEQ ID NO:3).

Example 4

Virus Isolation

In 2000, the samples were inoculated onto CEF and passaged five times. No cytopathic effects were observed in CEF cells. The fifth passage was processed for RT-PCR. Choanal swab samples were inoculated onto CEF for one hour, and the media was removed and replaced with MEM containing 1% fetal bovine serum, 100 units/ml penicillin G sodium, 100 µg/ml streptomycin sulfate, 150 µg/ml gentamicin, 0.292 mg/ml L-glutamine, 0.1 moles MEM non-essential amino acids.

Swab samples in MEM transport media were filtered through a 0.22 µm filter and inoculated by yolk sac route into seven-day-old eggs. The embryos were monitored daily for death and allantoic fluid collected at the time of embryo death or a maximum of five days post inoculation. The third passage of allantoic fluid was collected and analyzed by RT-PCR.

In 2001, virus isolation was attempted in 34 sample pools using CEF and SPF eggs. In addition, primary virus isolation was attempted using eleven sample pools in QT-35 cells (ATCC, Manassas, Va.). Choanal swab samples were inoculated onto CEF and QT-35 cells for one hour, and the transport media was removed and replaced with MEM containing 1% fetal bovine serum, 100 units/ml penicillin G sodium, 100 µg/ml streptomycin sulfate, 150 µg/ml gentamicin, 0.292 mg/ml L-glutamine, 0.1 moles MEM non-essential amino acids. The third passage of CEF and QT-35 cells were collected and analyzed for APV by RT-PCR. The RT-PCR positive tissue cultures were continued until passage five, inoculated into Vero cells (ATCC, Manassas, Va.) and monitored daily for cytopathic effect (CPE) consisting of patches of dead, sloughing cells and syncytia (multinucleated cells).

Swab samples in MEM transport media were filtered through a 0.22 µm filter and inoculated by yolk sac route into seven-day-old SPF eggs. The embryos were monitored daily for death and allantoic fluid collected at the time of embryo death or a maximum of five days post inoculation. The third passage of allantoic fluid was collected and analyzed by RT-PCR.

Example 5

Indirect Immunofluroescence Assay

Vero cells grown in a 96 well, flat-bottomed microtiter plate were inoculated with serial dilutions of each virus isolate and incubated for 48 hours. The cells were fixed with 100% cold ethanol for two minutes. The ethanol was removed and plate washed two times with phosphate buffered saline (PBS, pH 7.4 at 25° C.). The cells were covered with 4% paraformaldehyde (made in PBS) for 10 minutes and washed with PBS. Fifty microliters of hyperimmune turkey anti-APV serum diluted 1:320 in PBS containing 0.05% Tween 20 (Fisher Scientific, Fair Lawn, N.J.) and 0.3% BSA (Kirkegaard & Perry Laboratories, Gaithersburg, Md.) was added to each well and incubated overnight at 4° C. After incubation, the wells were washed with PBS containing 0.05% Tween 20 and 0.3% BSA. Fluorescein-labeled goat anti-turkey IgG conjugate (Kirkegaard & Perry Laboratories, Gaithersburg, Md.) was diluted 1:150 in PBS and added to each well for one hour, and washed with PBS-Tween-20 buffer. The plates were inverted and examined using fluorescent microscopy (wavelength=515 nm) (Jirjis et al., 2002, *J. Vet. Diagn. Invest.,* 14:172–5).

Example 6

Detection of APV in Canada Geese and Blue-Winged Teal

The results of the RT-PCR are shown in Table 1. In 2000, 13 of 19 juvenile and 25 of 33 adult Canada goose pools were RT-PCR positive for APV RNA. None of the adult Blue-winged teal pools were RT-PCR positive for APV RNA. Nine of 22 juvenile Blue-winged teal pooled samples were APV positive. The presence of virus in CEF cells was negative as determined by PCR from the $5^{th}$ blind passage. Virus isolation attempts following embryo yolk sac inoculation were negative as determined by RT-PCR of third allantoic fluid passage.

In 2001, 29 of 40 juvenile and 1 of 10 adult Canada goose pools were RT-PCR positive for APV RNA. Four of 18 juvenile Blue-wing teal pools were positive for APV and none of the 3 adult Blue-winged teal pools were positive for APV. Virus was isolated from five juvenile Canada goose choanal swab pools collected from the fifth passage of CEF, one of these same pools of field material yielded virus from QT-35 cells. Virus was not present following embryo yolk sac inoculation as determined by RT-PCR of third passage allantoic fluid.

TABLE 1

Results of APV RT-PCR on Choanal Swab Pools from Canada Geese and Blue-Winged Teal in 2000 and 2001

| Sample source | Year 2000 | Year 2001 |
|---|---|---|
| Adult Canada goose | 19/33[A] (75.8) | 1/10 (10.0) |
| Juvenile Canada goose | 13/19 (68.4) | 29/40 (72.5) |
| Adult Blue-winged teal | 0/9 (0.0) | 0/3 (0.0) |
| Juvenile Blue-winged teal | 9/22 (40.9) | 4/18 (22.2) |

[A]Data are displayed as the number of APV positive pools/number tested (percent positive in parenthesis).

When the five isolates from CEF were inoculated onto Vero cells, only four viruses adapted to Vero cell culture. Two of the Vero cell adapted isolates from Canada geese showed CPE including syncytia, the other two isolates replicated in cell culture without CPE. The presence of APV in Vero cells was confirmed by RT-PCR and immunofluorescence assay (IFA).

Because of the artificial flock conditions created by holding the birds for a length of time and because samples were pooled, these data cannot be used as in indicator of prevalence of APV in wild Canada geese populations. At the time of sampling, no wild geese presented clinical signs typical of an APV infection.

The Blue-winged teal sampling was conducted during the fall migration. During both years, teal were swabbed the same day they were captured so there were no artificial flock conditions created by holding the birds for several days. Because the swab samples were pooled, the results do not represent prevalence of APV in Blue-winged teal. In both years, the adult Blue-winged teal pools were negative, but APV positive pools were found in the juvenile birds. At the time of sampling, no Blue-winged teal presented clinical signs typical of an APV infection.

Example 7

Observations

Although yolk sac inoculation has been recommended for APV isolation, results herein indicate that direct inoculation of CEF was successful in detecting virus whereas embryo inoculation was not. In 51 attempts in 2000 and 2001, not a single isolate was obtained from embryo inoculation. All embryo inoculation took place at 7 days of development and the eggs were incubated for five days post inoculation. Gough et al. (2001, Vet. Record, 149:312) have reported using SPF eggs for APV isolation and allowing up to 11 days post inoculation to examine allantoic fluid. Gough et al. (2001, Vet. Record, 149:312) were unable to identify any virions using electron microscopy, but APV was isolated after inoculation of allantoic fluid onto pheasant and chicken embryo cell cultures. These results indicate APV may need a longer incubation time in embryos than previously thought.

The use of QT-35 cells has been reported to be useful in isolating APV, but in this study, only one virus isolate was detected in one of eleven of attempts compared to five of eleven attempts (made with the same sample pools) in CEF cells. The virus that was isolated in QT-35 cells was also isolated in CEF. In the study described herein, QT-35 cells apparently were less sensitive than CEF for primary isolation of APV.

Example 8

Vaccination of Turkeys With Canada Geese APV

Turkey poults were obtained from a commercial hatchery and were reared in isolation. At two weeks of age, all birds were bled to determine the status of APV antibodies using an ELISA test (Chiang et al., 2000, J. Vet. Diag. Invest., 12:381–4). 20 poults were inoculated with 200 $\mu$l of $1.0 \times 10^3$ $TCID_{50}$/ml of the avirulent Canada geese APV. Each bird was inoculated by administering 50 $\mu$l of the virus into each eye and each nostril of the birds. 20 poults were inoculated with mock-infected Vero cells (50 $\mu$l into each eye and nostril).

At four weeks of age (2 weeks post-vaccination), the birds were challenged with an APV/MN-2a virus that had been passaged 13 times (7 passages in CEF cells and 6 passages in Vero cells). The titer of the APV/MN-2a virus used to challenge vaccinated and non-vaccinated birds was $1.0\times10^{4.3}$ $TCID_{50}$/ml (Reed & Muench, 1938, *Am. J. Hyg.,* 27:493–7). The virus used to challenge vaccinated birds was originally isolated from nasal turbinates of 11-week-old turkeys and appeared to be more virulent than APV/MN-1a in preliminary studies. Each bird was challenged with 50 $\mu$l of virus in each eye and nostril (200 $\mu$l per bird). The birds were monitored daily for the appearance of clinical symptoms until the end of the study. Clinical scores were assigned according to the severity of clinical symptoms (Table 2). All birds were euthanized at 10 days post-challenge.

TABLE 2

Clinical Scoring for Signs of Experimental APV Infection

| | Clinical Score |
|---|---|
| Nasal Discharge | |
| Unilateral | 1 |
| Bilateral | 2 |
| Turbid | 3 |
| Watery Eyes | 1 |
| Sinus Swelling | 1 |

Example 9

Effectiveness of the Avirulent Canada Geese APV Vaccine

Following challenge, the non-vaccinated birds appeared initially depressed followed by development of clinical symptoms such as bilateral sinus swelling and bilateral nasal discharge. Clinical symptoms in the non-vaccinated birds started appearing 5 days post-challenge with maximum clinical symptoms observed 9–10 days post-challenge (29% of the non-vaccinated birds showed clinical symptoms).

Following challenge, 4% of the vaccinated birds showed clinical symptoms at 9–10 days post challenge, which generally were very mild (Table 3).

TABLE 3

Clinical scores after challenge with MN2a

| Days post challenge | Non-vaccinated | Vaccinated with MN 15a |
|---|---|---|
| 1 | 0.00 | 0.00 |
| 2 | 0.00 | 0.00 |
| 3 | 0.00 | 0.00 |
| 4 | 0.00 | 0.00 |
| 5 | 0.00 | 0.00 |
| 6 | 0.18 | 0.00 |
| 7 | 0.33 | 0/09 |
| 8 | 0.19 | 0.04 |
| 9 | 0.57 | 0.04 |
| 10 | 0.52 | 0.13 |
| 11 | .035 | 0.00 |
| 12 | .118 | 0.00 |
| 13 | 0 | 0.005 |
| 14 | 0 | 0.105 |

At 1 and 2 weeks post-vaccination, seroconversion was observed in vaccinated birds, although not all birds seroconverted. The birds in the non-vaccinated, non-challenged group remained negative for APV antibodies throughout the experiment, whereas birds in the non-vaccinated challenged group showed evidence of seroconversion 10 days post-challenge. See, Bennett et al., 2002, *Avian Disease*, 46:1025–9.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated avirulent Canada goose avian pneumovirus (aCg/APV).

2. The aCg/APV of claim 1, wherein said aCg/APV is designated APV/Canada goose/Minnesota/15a and is assigned ATCC Accession No. PTA-4840.

3. The aCg/APV of claim 1, wherein said aCg/APV is designated APV/Canada goose/Minnesota/15b and is assigned ATCC Accession No. PTA-4841.

4. The aCg/APV of claim 1, wherein said aCg/APV is designated APV/Canada goose/Minnesota/15c and is assigned ATCC Accession No. PTA-4842.

5. The aCg/APV of claim 1, wherein said aCg/APV is designated APV/Canada goose/Minnesota/15d and is assigned ATCC Accession No. PTA-4843.

6. A composition comprising an immunologically effective amount of the aCg/APV of claim 1.

7. The composition of claim 6, further comprising a pharmaceutically acceptable carrier.

8. The composition of claim 6, wherein said composition is effective for lowering the risk of an APV infection in poultry.

9. The composition of claim 8, wherein said poultry is selected from the group consisting of turkeys and chickens.

10. The composition of claim 8, wherein said poultry is a turkey.

11. The composition of claim 6, wherein said composition is effective for ameliorating the clinical signs of an APV infection in a challenged bird.

12. A method for preparing an aCg/APV comprising:

a) providing a Canada goose (Cg) APV; and b) identifying avirulent Cg (aCg) APV isolates.

13. The method of claim 12, wherein said Cg APV is isolated from host cells.

14. The method of claim 13, wherein said host cell is a non-avian cell.

15. The method of claim 14, wherein said host cell is a Vero cell.

16. The method of claim 12, wherein said aCg/APV is effective for reducing the incidence of the clinical signs of an APV infection in poultry.

17. The method of claim 16, wherein said poultry is selected from the group consisting of turkeys and chickens.

18. The method of claim 17, wherein said poultry is a turkey.

* * * * *

UNITED STATES PATENT AND TRADEMARK OFFICE
CERTIFICATE OF CORRECTION

PATENT NO. : 6,977,079 B2
APPLICATION NO. : 10/346542
DATED : December 20, 2005
INVENTOR(S) : Kakambi V. Nagaraja et al.

It is certified that error appears in the above-identified patent and that said Letters Patent is hereby corrected as shown below:

Title page, References Cited, Other Publications, third Cook et al. reference, after "of" please insert --an--;

Title page, References Cited, Other Publications, Cortese et al. reference, please delete "aginst" and insert --against--therefor;

Title page (Page 2), References Cited, Other Publications, Juhasz and Easton reference, please delete "Estensive" and insert --Extensive--therefor;

Title page (Page 2), References Cited, Other Publications, Kowk and Higuchi reference, please delete "Kowk" and insert --Kwok--therefor;

Title page (Page 3), References Cited, Other Publications, Roy et al. reference, please delete "2764" and insert --2674--therefor;

Title page (Page 3), References Cited, Other Publications, fourth Shin et al. reference, please delete "form" and insert --from--therefor.

Signed and Sealed this

First Day of August, 2006

JON W. DUDAS
*Director of the United States Patent and Trademark Office*